United States Patent
Kuperman et al.

[19]

[11] Patent Number: 6,061,586
[45] Date of Patent: May 9, 2000

[54] DEVICE AND METHOD FOR ASSESSING DRUG LEVELS WITHIN PHYSIOLOGICAL FLUIDS

[75] Inventors: Igor Kuperman, Yokneam; Alexander Zusmanovitch, Haifa, both of Israel

[73] Assignee: AMS-Advanced Monitoring Systems Ltd., Migdal Haemek, Israel

[21] Appl. No.: 08/974,842

[22] Filed: Nov. 20, 1997

[51] Int. Cl.$^7$ ........................................ A61B 5/05
[52] U.S. Cl. ..................... 600/349; 600/573; 600/584
[58] Field of Search ........................... 600/309, 345, 600/349, 362, 573, 584; 604/1, 187; 436/178

[56] References Cited

U.S. PATENT DOCUMENTS

| | | | |
|---|---|---|---|
| 4,114,605 | 9/1978 | McGhee et al. | 600/573 |
| 4,635,488 | 1/1987 | Kremer | 600/573 |
| 4,834,110 | 5/1989 | Richard | 600/573 |
| 4,895,808 | 1/1990 | Romer | 436/178 |
| 5,056,521 | 10/1991 | Parsons et al. | 600/573 |
| 5,260,031 | 11/1993 | Seymour | 600/573 |
| 5,573,009 | 11/1996 | Thieme et al. | 600/573 |

OTHER PUBLICATIONS

Ben–Aryeh et al, "Saliva for Monitoring of Patients with Primary Affective Disorders", *Is. J. Med. Sci.*, vol. 20, pp. 197–200, 1984.

Terao et al, "A Further Prospective Evaluation of an Equation to Predict Daily Lithium Dose", *J. Clin. Psychiatry*, vol. 56, No. 5, pp. 193–195, 1995.

Campbell et al, "An Update on the Use of Lithium Carbonate in Aggressive Children and Adolescents with Conduct Disorder", *Psychopharmacology Bul.*, 31(1): 93–102, 1995.

Gellenberg, et al, "The Meaning of Serum Lithium Levels in Maintenance Therapy of Mood Disorders: A Review of the Literature", *J. Clin. Psychiatry*, vol. 50, No. 12(Supp), pp. 17–47, 1989.

Srinivasan et al, "Insant Lithium Monitoring: A Clincal Revolution in the Making", *Brit. J. Clin. Practice*, vol. 50, No. 7, pp. 387–388, 1996.

Jefferson, J.W., Chairperson, "Lithium: The Present and the Future", *J. Clin. Psychiatry*, vol. 56, No. 1, 41–48, 1995.

*Primary Examiner*—Cary O'Connor
*Assistant Examiner*—Ryan Carter
*Attorney, Agent, or Firm*—Mark M. Friedman

[57] ABSTRACT

A device for monitoring the concentration of a chemical component within a patient's physiological fluid is provided, comprising: (a) an electrode assembly for immersion within a patient's saliva, including: a ion selective electrode and a reference electrode for providing a voltage signal; and an interface element for electrically connecting the electrode assembly to a microprocessor; (b) a cup for accommodating a volume of a patient's saliva; (c) a stand element for holding the electrode assembly at a predetermined position with relation to the cup; and (d) a microprocessor for processing the voltage signal, the microprocessor determining the concentration of the chemical component within the volume of saliva and calculates the concentration of the chemical component within the physiological fluid according to a selected mathematical model. Further according to the present invention there is provided a sampling kit for collecting a predetermined volume of a patient's saliva, including: (a) a syringe-like element, including: (i) a substantially elongated tubular member; (ii) a substantially elongated piston member for insertion into the tubular member; and (b) a sponge member for absorbing the patient's saliva, the sponge member for insertion into the tubular member, the sponge member being compressible by means of the piston member so as to enable extraction of the patient's saliva therefrom into a collecting cup.

24 Claims, 4 Drawing Sheets

DEVICE AND METHOD FOR ASSESSING DRUG LEVELS WITHIN PHYSIOLOGICAL FLUIDS

FIELD AND BACKGROUND OF THE INVENTION

The present invention relates to device and method for assessing drug levels within physiological fluids and, more particularly to apparatus and method for assessing lithium concentration within a patient's blood based on lithium concentration measured within the patient's saliva.

Lithium carbonate is a drug commonly used in the treatment of acute manias and depression syndromes. The therapeutic range of lithium in serum is about 0.4–1.2 meq/L. Serious lithium toxicity occurs at slightly higher serum levels (at least about 1.5 meq/L). The monitoring of lithium concentration within the blood is necessary for ensuring the safety of such treatment and to avoid toxicity. Thus, Lithium levels within the blood should be monitored frequently during the course of treatment, especially until a stable therapeutic level of lithium is reached.

Currently, the monitoring of lithium concentration within the blood involves a lengthy procedure which requires the employment of expensive equipment and professional operators for operating such equipment. A blood sample is extracted from the patient by a family doctor or a nurse. The extracted blood is collected within a sample tube. Following the addition of an anti-clotting material, the sample tube is transferred to a laboratory for analysis. At the laboratory, the plasma of the blood sample is separated from the blood cells by means of a centrifuge. The plasma is then transferred to another tube and is then analyzed by means of a flame photometer. The flame photometer is an expansive and cumbersome device which requires a professional operator. Further, the flame photometer is expensive to operate and has to be specifically prepared and calibrated prior to each examination. As a result, such device is usually activated only once or twice a week, after a substantial amount of blood samples have been collected. Following analysis of the blood sample, a written result is sent to the office and then to the family doctor. Such lengthy process (which may be extended for more than one week) may be ineffective in the sense that it does not provide an immediate feedback in the event of toxicity. Toxic levels of lithium within the patient's blood may occur as a result of introduction of over-dosage of the drug, or in the event of impaired clearance of the drug owing to damaged kidney or damaged liver. Lithium concentration within the blood is also dependent on hormonal regulation and other physiological factors and therefore may feature abnormal profile when the patient suffers from hormonal or other physiological problems. An immediate feedback is extremely important when treating children since relatively low concentrations of lithium may cause toxicity. Since there is no current effective treatment for lithium poisoning, an immediate feedback relating to lithium concentration within the blood is essential.

None of the prior art methods and devices provide substantially immediate feedback relating to lithium levels within the patient's blood and therefore such methods and devices are ineffective in detecting toxicity on time.

Further, none of the prior art methods and devices enables a doctor to independently conduct lithium concentration examinations without the need to use expensive and cumbersome equipment such as a flame photometer; without the need to send blood samples to laboratories equipped with such equipment; and without the need to employ professional operators for operating such equipment.

Further, none of the prior art methods and devices provides a non-invasive approach for monitoring lithium concentration within a patient's blood during a predetermined period of time.

There is thus a widely recognized need for, and it would be highly advantageous to have, method and device which provide substantially immediate feedback relating to lithium concentration within a patient's blood so as to effectively detect toxicity conditions on time.

It would be further advantageous to have such method and device which enable a doctor or a patient to independently conduct lithium concentration examinations without the need to use expensive and cumbersome equipment such as a flame photometer; without the need to end blood samples to laboratories equipped with such equipment; and without the need to employ professional operators for operating such equipment.

It would be further advantageous to have such method and device which enable to conduct such lithium concentration examinations non-invasively.

SUMMARY OF THE INVENTION

According to the present invention there is provided a device for monitoring the concentration of a chemical component within a patient's physiological fluid, comprising: (a) an electrode assembly for immersion within a patient's saliva, including: a ion selective electrode and a reference electrode for providing a voltage signal representative of the potential drop between the ion selective electrode and the reference electrode; and an interface element for electrically connecting the electrode assembly to a microprocessor; (b) a cup for accommodating a volume of a patient's saliva; (c) a stand element for holding the electrode assembly at a predetermined position with relation to the cup; and (d) a microprocessor for processing the voltage signal, the microprocessor determines the concentration of said chemical component within the volume of saliva according to the voltage signal and calculates the concentration of said chemical component within the physiological fluid according to a selected mathematical model.

According to further features in preferred embodiments of the invention described below, the device further includes a selective membrane connected to the ion selective electrode for specifically allowing the passage of said chemical component therethrough.

Preferably, the device includes a display element and a printer electrically connected to said microprocessor. The stand element is preferably automatically handled by means of the microprocessor. The electrode assembly may include a processing element for initial processing of said voltage signal. The processing element may include an amplifier and an analog to digital converter.

Further according to the present invention there is provided a sampling kit for collecting a predetermined volume of a patient's saliva, including: (a) a syringe-like element, including: (i) a substantially elongated tubular member having an upper opening and a lower opening; (ii) a substantially elongated piston member for insertion into the tubular element through the upper opening; and (b) a sponge member for absorbing the patient's saliva, the sponge member for insertion into the tubular member, the sponge member being compressible by means of the piston member so as to enable extraction of the patient's saliva therefrom.

Preferably, the piston member includes a substantially elastic portion so as to enable sealing of the upper aperture of the tubular member. Further, the tubular member preferably includes a sealing member for sealing the lower opening of the tubular member.

Further according to the present invention there is provided a method of monitoring the concentration of a chemical component within a patient's physiological fluid, comprising: (a) immersing an electrode assembly within a patient's saliva, the electrode assembly including: (i) a ion selective electrode; and (ii) a reference electrode; (b) providing a voltage signal representative of the potential drop between the ion selective electrode and the reference electrode; (c) sending the voltage signal to a microprocessor; (d) determining the concentration of the chemical component within the patient's saliva by means of the microprocessor based on said potential drop; and (e) calculating the concentration of the chemical component within the physiological fluid according to a selected mathematical model.

According to further features in preferred embodiments of the invention described below, the mathematical model may be:

$$[C]_{fluid}=0.13+0.36\times[C]_{saliva},$$

wherein: $[C]_{fluid}$ is the concentration of said chemical component within the patient's physiological fluid; and $[C]_{saliva}$ is the concentration of said chemical component within the patient's saliva.

Alternatively, the mathematical model is: $[C]_{fluid}=K\times[C]_{saliva}$, wherein: $[C]_{fluid}$ is the concentration of said chemical component within the patient's physiological fluid; $[C]_{saliva}$ is the concentration of said chemical component within the patient's saliva; and K is a specific factor determined for a specific patient. Preferably, K is determined based on previous reference measurements of $[C]_{fluid}$ and $[C]_{saliva}$.

Further according to the present invention there is provided a method of collecting a patient's saliva, comprising: (a) absorbing a patient's saliva by means of a sponge member introduced into the patient's mouth; (b) introducing the sponge member into a syringe-like element, including: (i) a substantially elongated tubular member having an upper opening and a lower opening; (ii) a substantially elongated piston member for insertion into the tubular member through the upper opening; (c) pushing the sponge member along the tubular member by means of the piston member; (d) squeezing the sponge member by means of the piston member; and (e) collecting the saliva extracted from the sponge member within a cup.

Preferably, the chemical component is lithium and the physiological fluid is saliva.

The present invention successfully addresses the shortcomings of the presently known configurations by providing method and device which provide substantially immediate feedback relating to lithium concentration within a patient's blood so as to effectively detect toxicity conditions on time.

Further, the present invention addresses the shortcomings of the presently known configurations by providing method and device which enable a doctor or a patient to independently conduct lithium concentration examinations without the need to use expensive and cumbersome equipment such as a flame photometer; without the need to send blood samples to laboratories equipped with such equipment; and without the need to employ professional operators for operating such equipment.

Further, the present invention addresses the shortcomings of the presently known configurations by providing method and device which enable to conduct such lithium concentration examinations non-invasively.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of method and device for determining the concentration of a chemical component within physiological fluids of a patient according to the concentration of the chemical component measured within the patient's saliva. Specifically, the present invention is of method and device for assessing the lithium concentration within a patient's blood according to the lithium concentration measured within the patient's saliva. Method and device according to the present invention enable substantially immediate feedback relating to the lithium concentration within the patient's blood by using relatively simple equipment and procedure, thereby enabling a family doctor or a patient to independently conduct such lithium concentration examination.

Although the invention is herein described with reference to lithium concentration within the patient's blood, it may be used for assessing the concentration of any chemical component within any physiological fluid of the patients (e.g., lymphatic fluid) based on a given mathematical relationship.

The principles and operation of apparatus and method according to the present invention may be better understood with reference to the drawings and the accompanying description.

Figure 1:
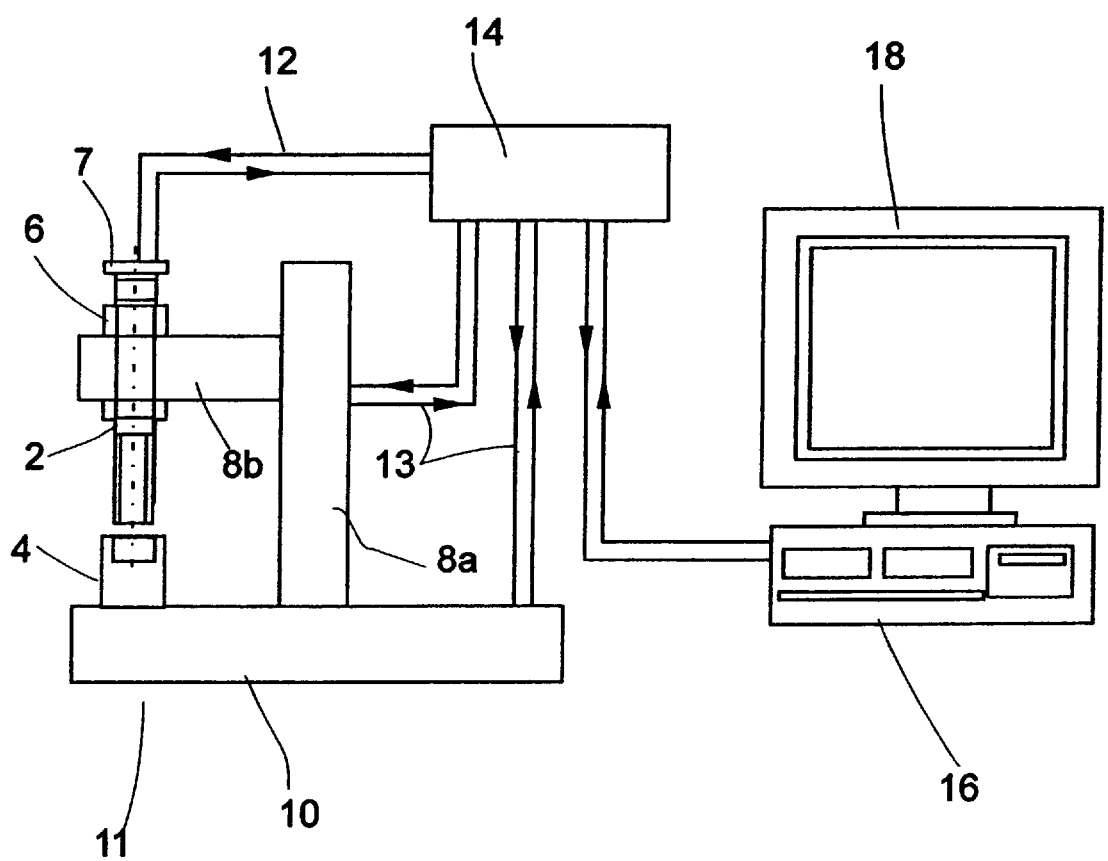
FIG. 1 is a schematic view of a device according to the present invention.
Figure 2:
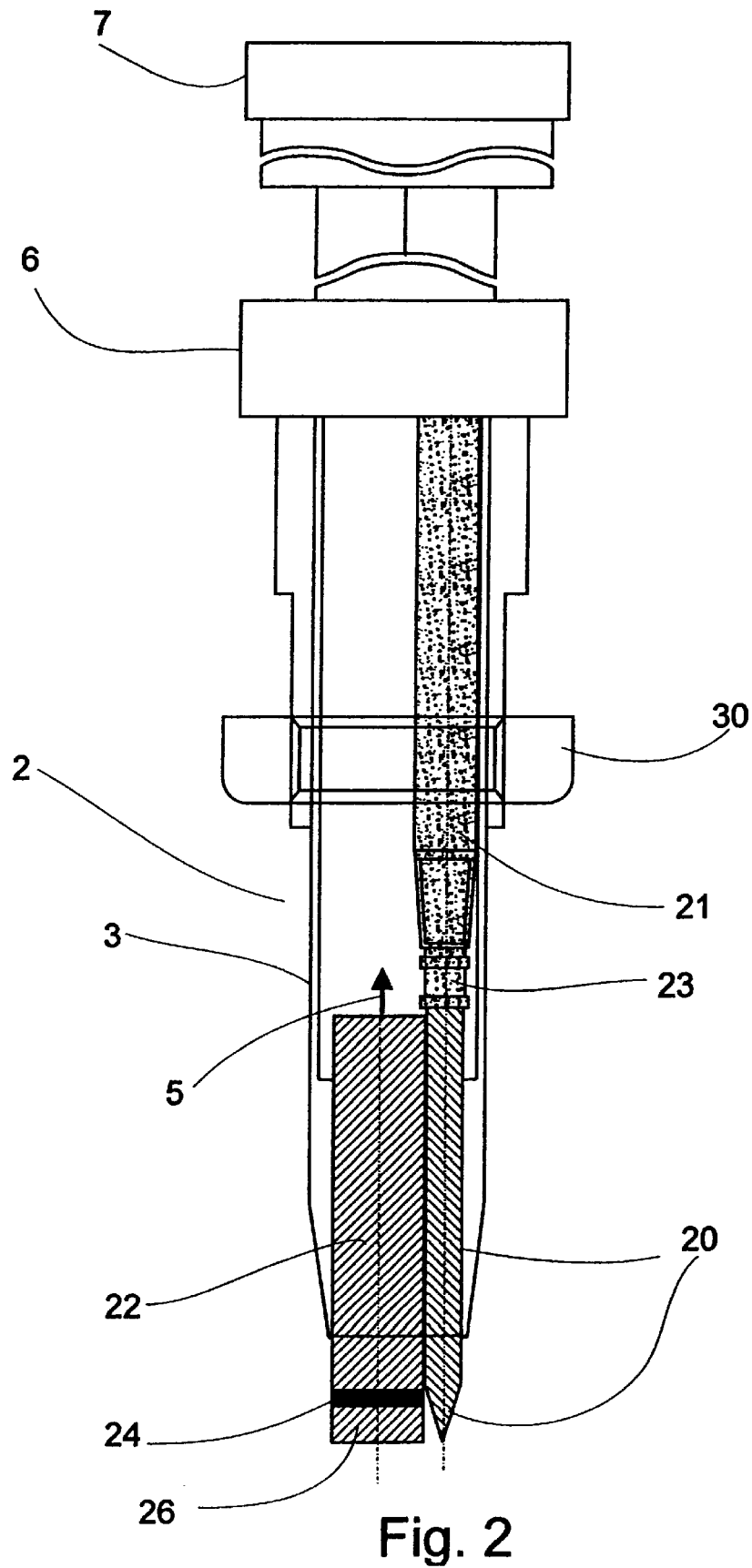
FIG. 2 is an enlarged view of an electrode assembly according to the present invention.

Referring now to the drawings, FIGS. 1 and 2 illustrates a device according to the present invention. As shown in the figures, the device includes an electrode assembly 2 for measuring the concentration of a chemical component such as lithium within a patient's saliva according to the potential drop measured between a ion selective electrode 22 and a reference electrode 20, wherein ion selective electrode 22 specifically bind the chemical component. As shown in FIG. 2, ion selective electrode 22 and reference electrode 20 are accommodated within a housing 3 and are immersed within a cup 4 containing a saliva sample from a patient. Reference electrode 20 is preferably connected to a container 21 including a reference solution by means of a connector element 23. Further, container 21 is preferably held within housing 3 by means of an electrode holder 30. Ion selective electrode 22 preferably includes a selective membrane 26 which specifically enables the passage of lithium therethrough, the membrane being connected to ion selective electrode 22 by means of a solid contact connector 24. As shown, ion selective electrode 22 is preferably inserted into housing 3 as indicated by arrow 5. Electrode assembly 2 further includes a processing element 6 for initial processing of the voltage signal obtained by the potential drop measured between ion selective electrode 22 and reference electrode 20. Processing element 6 preferably includes an amplifier for amplifying the voltage signal and an analog to digital converter for converting such analog voltage signal to a digital signal. Further, electrode assembly 2 further includes an interface 7 for connecting electrode assembly 2 to a microprocessor 16 by means of electrical wires 12.

As shown in FIG. 1, electrode assembly 2 is preferably held at a predetermined height above cup 4 by means of a stand element 11. Stand element 11 preferably includes a holding member 8b for holding electrode assembly 2, the holding member being movable along a shaft member 8a anchored to a support member 10. Cup 4 is positioned on support member 10 so as to allow immersion of ion selective electrode 22 and reference electrode within the patient's saliva.

Preferably, stand 11 includes an automatically operated mechanical system. Accordingly, holding member 8b and shaft member 8a as well as support member 10 are preferably electrically connected to microprocessor 16 by means of electrical wires 13 so as to allow automatic handling of member 8b with reference to support member 10, thereby accurately positioning electrode assembly 3 above cup 4 and appropriately immersing electrodes 20 and 22 within the patient's saliva.

Microprocessor 16 preferably includes a software card (schematically denoted as 14) for manipulating the device according to predetermined requirements. Specifically, software card 14 may include various algorithms for calculating the lithium concentration within the patient's blood according to the lithium concentration measured by electrode assembly 3.

As shown in FIG. 1, a device according to the present invention further includes a display element 18 for displaying the results of a current test as well as results of previous tests or any other parameters related to the medical record of a specific patient. An alarm signal may indicate that a toxic level of lithium has been identified, or that a substantially low level of lithium has been identified. The device may further include a printer (not shown) for providing written results.

A preferred algorithm for calculating lithium concentration within a patient's blood according to the lithium concentration measured within the patient's saliva may be as follows:

$$[Li]_{blood} = 0.13 + 0.36 \times [Li]_{saliva}.$$

The above mathematical model, which is well known in the art, shows the advantage of saliva tests over blood tests. Specifically, the lithium concentration within a patient's saliva is amplified with relation to the lithium concentration within the patient's blood. Thus, saliva tests may provide greater accuracy relative to blood tests owing to such physiological amplifying effect.

Alternatively, reference measurements of lithium concentrations within the patient's blood and saliva may be conducted so as to determine a specific factor for a specific patient according which future analyses are performed. For example, if according to the reference measurements a factor K is obtained, wherein: $[Li]_{blood} = K \times [Li]_{saliva}$, then such factor is used for assessing future lithium concentrations within the patient's blood based on respective lithium concentrations measured within the patient's saliva.

Further according to the present invention, there is provided a sampling kit for taking saliva samples, which kit enabling to effectively and efficiently perform the above measurements. Preferably, a device according to the present invention is provided with a set of disposable sampling kits at different sizes.

Figure 3:
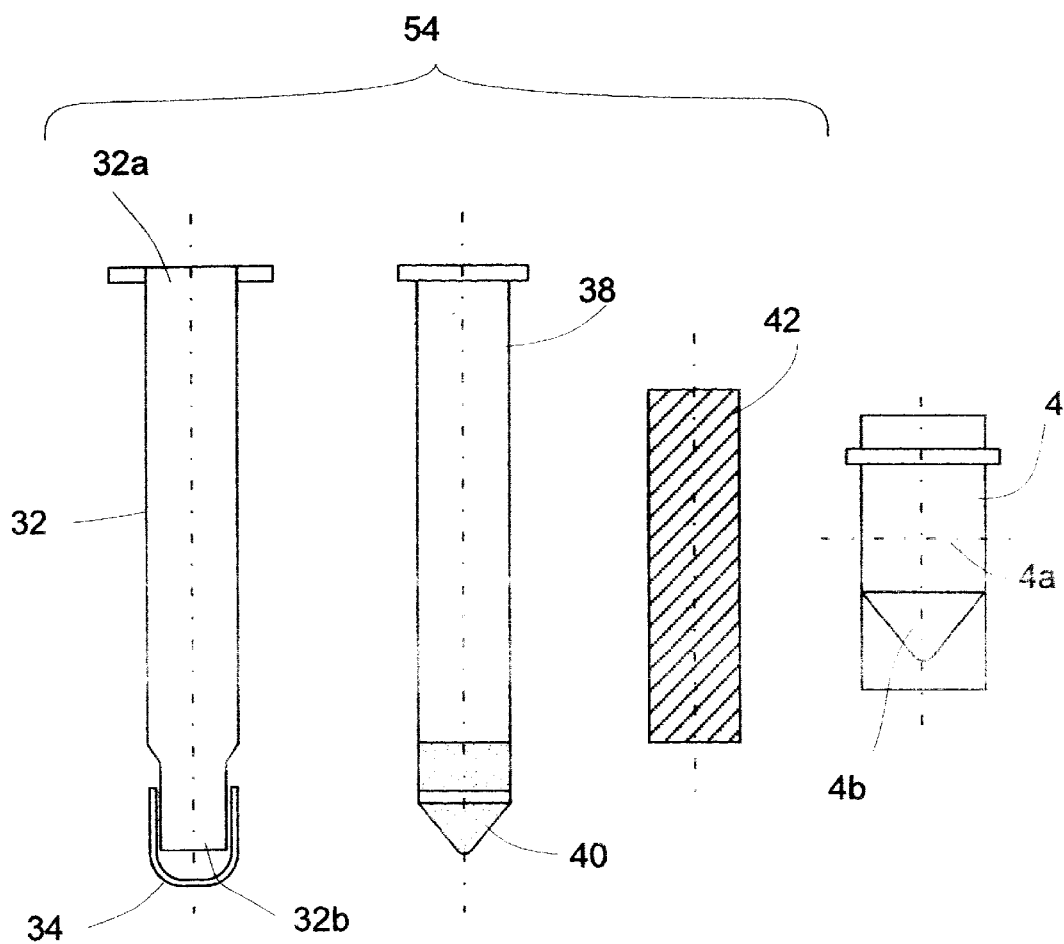
FIG. 3 is a schematic view of a sampling kit according to the present invention.
Figure 4:
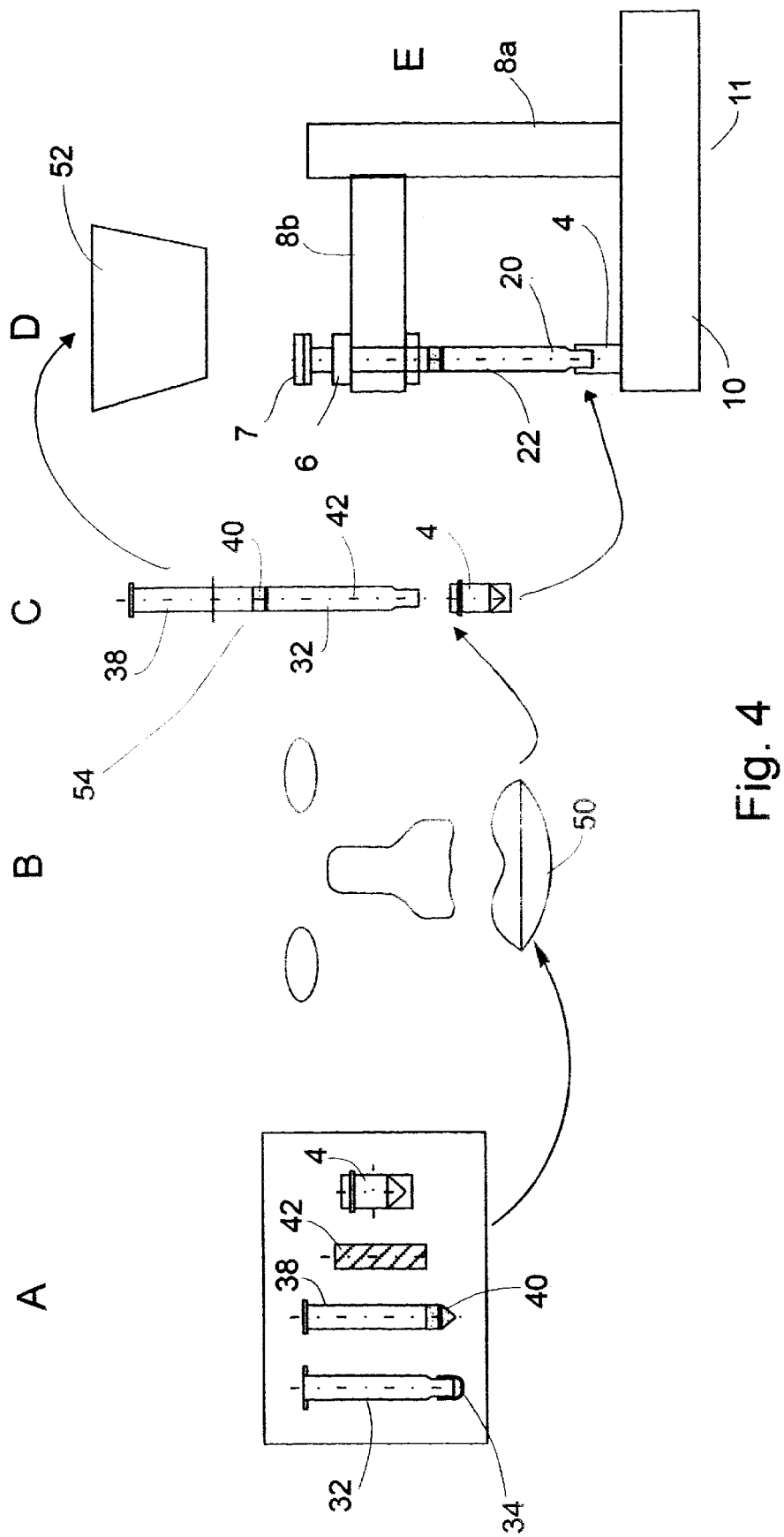
FIG. 4 is a schematic view of a method according to the present invention.

As shown in FIGS. 3 and 4, a sampling kit according to the present invention preferably comprises: a disposable syringe-like element 54, including: (i) an elongated tubular element 32 having an upper opening 32a and a lower opening 32b, the lower opening being sealable by means of a sealing element 34; (ii) an elongated piston element 38 for insertion into elongated tubular element 32, the piston element having a substantially elastic member 40 connected to its lower end; and (iii) a sponge member 42 for absorbing a patient's saliva, the sponge member for insertion into tubular element 32, the sponge element being compressible by means of piston element 38. Further, a sampling kit according to the present invention preferably includes a cup 4 having a conic portion 4b for effectively collecting the patient's saliva extracted from sponge 42, and a marker 4a for enabling the collection of a predetermined volume of saliva (preferably about 1 ml).

As shown in FIG. 4, the patient places sponge 42 within his mouth 50 for several minutes so as to allow absorption of saliva. Preferably, when sponge 42 is substantially saturated with saliva, the patient inserts sponge 42 into tubular element 32 and slightly pushes the sponge by means of piston element 38 so as to seal the upper opening 32a of tubular element 32. The lower opening 32b of tubular element 32 is sealed by means of sealing element 34, thereby providing effective sealing to disposable syringe-like element 54. Thus, syringe-like element 54 may be kept at cooling conditions for a required period of time.

Preferably, the test is immediately preformed by a family doctor (or a nurse) during a conventional visit. The family doctor places syringe-like element 54 above cup 4. He then removes sealing element 34 from the lower portion of tubular element 32, and presses piston element 38 into tubular element 32 so as to squeeze sponge member 42 and collect the extracted patient's saliva within cup 4. The saliva collected within cup 4 is relatively clean from food particles due to filtration by sponge member 42. Tubular element 32, piston element 38 and sponge member 42 are discarded e.g., a waste container 52.

The doctor then places cup 4 at appropriate position on supporting member 10 of stand 11. Automatic calibration and handling of members 8b and 8a with reference to support member 10 enable accurate positioning of electrode assembly 3 above cup 4 so as to appropriately immersing electrodes 20 and 22 within the patient's saliva.

The measurement results are preferably obtained within several minutes. Such results preferably include the lithium concentration measured within the patient's saliva as well as the calculated lithium concentration within the patient's blood, wherein the calculation is preferably performed according to one of the above procedures. The results are preferably displayed on display element 18 and printed by means of a printer (not shown), so as to allow immediate feedback to the family doctor.

While the invention has been described with respect to a limited number of embodiments, it will be appreciated that many variations, modifications and other applications of the invention may be made.

What is claimed is:

1. A device for monitoring the concentration of a chemical component within a patient's physiological fluid, comprising:

(a) an electrode assembly for immersion within a patient's saliva, including: a ion selective electrode and a reference electrode for providing a voltage signal representative of the potential drop between said ion selective electrode and said reference electrode; and an interface element for electrically connecting said electrode assembly to a microprocessor;

(b) a cup for accommodating a volume of a patient's saliva;

(c) a stand element for holding said electrode assembly at a predetermined position with relation to said cup; and (d) a microprocessor for processing said voltage signal, said microprocessor determines the concentration of said chemical component within said volume of saliva according to said voltage signal and calculates the concentration of said chemical component within said physiological fluid according to a selected mathematical model.

2. The device of claim 1, further including a selective membrane connected to said ion selective electrode for specifically allowing the passage of said chemical component therethrough.

3. The device of claim 1, further comprising a display element electrically connected to said microprocessor.

4. The device of claim 1, further comprising a printer electrically connected to said microprocessor.

5. The device of claim 1, wherein said stand element is automatically handled by means of said microprocessor, said stand element being electrically connected to said microprocessor.

6. The device of claim 1, wherein said electrode assembly includes a processing element for initial processing of said voltage signal.

7. The device of claim 1, wherein said microprocessor includes an amplifier.

8. The device of claim 1, wherein said microprocessor includes an analog to digital converter.

9. The device of claim 1, further comprising a set of sampling kits, each of said sampling kits including:
   (a) a syringe-like element, including:
      (i) a substantially elongated tubular member having an upper opening and a lower opening;
      (ii) a substantially elongated piston member for insertion into said tubular element through said upper opening; and
   (b) a sponge member for absorbing the patient's saliva, said sponge member for insertion into said tubular member, said sponge member being compressible by means of said piston member so as to enable extraction of the patient's saliva from said sponge member.

10. The device of claim 9, wherein said piston member includes a substantially elastic portion so as to enable sealing of said upper aperture of said tubular member.

11. The device of claim 9, wherein said tubular member includes a sealing member for sealing said lower opening.

12. The device of claim 1, wherein said cup includes a marker for enabling the collection of a predetermined volume of saliva within said cup.

13. The device of claim 9, wherein said sampling kit is disposable.

14. The device of claim 1, wherein said cup is disposable.

15. A method of monitoring the concentration of a chemical component within a patient's physiological fluid, comprising:
   (a) immersing an electrode assembly within a patient's saliva, said electrode assembly including:
      (i) a ion selective electrode; and
      (ii) a reference electrode;
   (b) providing a voltage signal representative of the potential drop between said ion selective electrode and said reference electrode;
   (c) sending said voltage signal to a microprocessor;
   (d) determining the concentration of said chemical component within the patient's saliva by means of said microprocessor based on said potential drop; and
   (e) calculating the concentration of the chemical component within the physiological fluid according to a selected mathematical model.

16. The method of claim 15, wherein said mathematical model is:

$$[C]_{fluid} = 0.13 + 0.36 \times [C]_{saliva},$$

wherein:
   $[C]_{fluid}$ is the concentration of said chemical component within the patient's physiological fluid; and
   $[C]_{saliva}$ is the concentration of said chemical component within the patient's saliva.

17. The method of claim 15, wherein said mathematical model is:

$$[C]_{fluid} = K \times [C]_{saliva},$$

wherein:
   $[C]_{fluid}$ is the concentration of said chemical component within the patient's physiological fluid;
   $[C]_{saliva}$ is the concentration of said chemical component within the patient's saliva; and
   K is a specific factor determined for a specific patient.

18. The method of claim 17, wherein K is determined based on previous reference measurements of $[C]_{fluid}$ and $[C]_{saliva}$.

19. The method of claim 15, wherein said chemical component is lithium.

20. The method of claim 15, wherein said physiological fluid is blood.

21. The method of claim 15, further comprising: providing an alarm signal when the concentration of said chemical component within said physiological fluid is above a maximal threshold.

22. The method of claim 15, further comprising: providing an alarm signal when the concentration of said chemical component within said physiological fluid is below a minimal threshold.

23. The method of claim 15, further comprising: a step of collecting the patient's saliva, including:
   (a) absorbing a patient's saliva by means of a sponge member introduced into the patient's mouth;
   (b) introducing said sponge member into a syringe-like element, including:
      (i) a substantially elongated tubular member having an upper opening and a lower opening;
      (ii) a substantially elongated piston member for insertion into said tubular member through said upper opening;
   (c) pushing said sponge member along said tubular member by means of said piston member;
   (d) squeezing said sponge member by means of said piston member; and
   (e) collecting the saliva extracted from said sponge member by within a cup.

24. The method of claim 17, wherein said piston member includes an elastic portion so as to enable sealing of said upper opening, and wherein said tubular member includes a sealing member for sealing said lower opening, so as to enable preserving of the patient's saliva.

* * * * *